United States Patent [19]

Goldhorn et al.

[11] Patent Number: 5,044,354
[45] Date of Patent: Sep. 3, 1991

[54] APPARATUS FOR TREATING A LIFE FORM WITH FOCUSSED SHOCKWAVES

[75] Inventors: Klaus Goldhorn, Erlangen; Hans P. Seubert, Heroldsbach, both of Fed. Rep. of Germany

[73] Assignee: Siemens Aktiengesellschaft, Munich, Fed. Rep. of Germany

[21] Appl. No.: 546,526

[22] Filed: Jun. 29, 1990

[30] Foreign Application Priority Data

Jun. 30, 1989 [EP] European Pat. Off. ......... 89111988.5
Jun. 30, 1989 [DE] Fed. Rep. of Germany ... 8908037[U]

[51] Int. Cl.$^5$ .............................................. A61B 17/22
[52] U.S. Cl. ............................... 128/24 EL; 378/196; 378/198
[58] Field of Search ................. 378/196, 197, 209; 128/653 A, 24 EL; 269/322, 323, 324, 325, 326, 328

[56] References Cited

U.S. PATENT DOCUMENTS

| | | | |
|---|---|---|---|
| 4,426,725 | 1/1984 | Grady | 378/196 |
| 4,674,505 | 6/1987 | Pauli et al. | |
| 4,796,613 | 1/1989 | Heuman et al. | 128/24 EL |
| 4,869,239 | 9/1989 | Krauss et al. | 128/24 EL |
| 4,872,193 | 10/1989 | Elff et al. | |
| 4,877,017 | 10/1989 | Hahn et al. | 128/24 EL |
| 4,928,672 | 5/1990 | Grasser et al. | |

FOREIGN PATENT DOCUMENTS 009858 8/1988 Fed. Rep. of Germany.

OTHER PUBLICATIONS

Dornier Medizintechnik Brochure for "Dornier Lithotripter MPL 9000".
Philips Company Brochure for "MFL 5000".

Primary Examiner—Lee S. Cohen
Assistant Examiner—Scott R. Akers
Attorney, Agent, or Firm—Hill, Van Santen, Steadman & Simpson

[57] ABSTRACT

An apparatus for treating a life form with focused shockwaves has a patient bed, a locating system and a shockwave source, as apparatus components with which shockwaves converging in a focal region that coincides with a therapeutically relevant region located with the locating system can be generated. A common, essentially horizontally proceeding swiveling axis is provided around which the apparatus components are optionally pivotable independently of one another or around which at least two of the apparatus components are pivotable synchronously.

26 Claims, 9 Drawing Sheets

APPARATUS FOR TREATING A LIFE FORM WITH FOCUSSED SHOCKWAVES

BACKGROUND OF THE INVENTION

1. Field of the Invention

The invention is directed to an apparatus for treating a patient (human or animal) with focussed shockwaves which includes a patient bed and a shockwave source, the shockwave source being adjustable relative to the patient bed the apparatus also including means for acoustically coupling shockwaves to the patient that converge in a focal region lying on the acoustic axis of the shockwave source.

2. Description of the Prior Art

Devices of the type described above are currently employed for non-invasive disintegration of calculi situated inside the body, for example, kidney stones or gall stones. Their use has also been proposed in conjunction with healing or treating other pathologies, for example in tumor therapy or in treating vessel diseases.

An apparatus of the type initially cited that serves for the non-invasive disintegration of calculi situated in the body of a life form is described in the publication of Dornier Medizintechnik, "Dornier Lithotripter MPL 9000". The position of the calculus to be disintegrated is identified with a locating means and the calculus is subsequently brought into the focal region of the shockwaves by adjusting the shockwave source and the patient bed relative to one another. Under the action of a sequence of shockwaves generated with the shockwave source, the calculus disintegrates into fine fragments that can be eliminated naturally. In order to be able to align the patient in the required way, the patient bed is pivotable around the horizontal axis that proceeds transversely relative to the longitudinal axis of the patient bed. Further, the shockwave source is isocentrically adjustable with reference to the focal region of the shockwaves, i.e. the shockwave source is adjustable on a section of a spherical shell whose center lies in the focal region.

Particularly when disintegrating gall stones, a problem arises that the stones continuously change their position under the action of the shockwaves. When this is the case, an attempt must be made to bring the patient into such an inclined position by adjusting the patient bed so that the stones assume a stable position under the influence of the force of gravity, and thus retain this position under the influence of the shockwaves as well. This can be inherently achieved in the known apparatus by pivoting the patient bed around the horizontal axis so that, corresponding to the requirement of the therapy, the patient is brought either into a position wherein his head lies lower than his feet or into a position wherein his feet lie lower than his head. However, dislocations of the patient bed and shockwave source relative to one another thereby occur such that the calculi are then no longer situated in the focal region of the shockwaves. It is thus necessary to again locate the calculi before continuing the treatment and, by adjusting the patient bed, to again align the patient such that the calculi are situated in the focal region.

Devices of the type initially described are also known include a locating means adjustable relative to the other apparatus components for locating of a therapeutically relevant region, for example, a calculus, to which the target area of the shockwave generator is aligned. A device of this type is described in the publication of the Philips Company, C. H. F. Mueller, Medizinisch-Technische Systeme, "MFL 5000—Der Urologische Arbeitsplatz fuer Diagnose und Therapie". The position of the therapeutically relevant region, i.e. of the calculus to be disintegrated, is identified with an x-ray locating means and the calculus is subsequently brought into the focal region of the shockwaves by adjusting the patient bed relative to the shockwave source and relative to the locating means. Under the action of a sequence of shockwaves generated with the shockwave source, the calculus disintegrates into fine fragments that can be eliminated naturally. In the case of the known apparatus, the x-ray locating means includes an x-ray radiator and a radiation receiver in the form of an x-ray image intensifier that are attached to opposite ends of a U-shaped arc that is in turn attached to a stand pivotable around a horizontal axis. The intersection of the central ray of the x-ray locating means with the horizontal axis corresponds to the position of the focal region of the shockwaves. The shockwave source is pivotably attached such to an axis inclined relative to the vertical that proceeds through the intersection of the central ray with the horizontal axis that its central ray always proceeds through the said intersection and its focal region assumes the said position. In order to be able to align the patient in the required way, the patient bed, among other things, is pivotable around a further horizontal axis that proceeds transversely relative to the longitudinal axis of the patient bed.

As already explained, an attempt may potentially have to be made, particularly when disintegrating gall stones, to bring the patient into such an inclined position by adjusting the patient bed that the calculi assume a stable position under the influence of the force of gravity, retaining this stable position under the influence of the shockwaves as well. This can be achieved by pivoting the patient bed around the further horizontal axis in that the patient is brought into a position with elevated feet or, respectively, elevated pelvis. As described above, displacements of the patient bed relative to the shockwave source and relative to the x-ray location means occur so that the calculi are no longer situated in the focal region of the shockwaves. It is thus necessary to again locate the calculi before continuing the treatment and to align the patient such that the calculi are again situated in the focal region of the shockwaves.

SUMMARY OF THE INVENTION

An object of the invention is to provide an apparatus for treating a life form with focussed shockwaves such as an extracorporeal lithotripsy apparatus wherein the alignment of the shockwave source to the target region is preserved when pivoting the patient bed.

This object is achieved in accordance with the principles of the present invention in an apparatus wherein a common swiveling axis is provided around which the apparatus components can be optionally swiveled independently of one another or synchronously. As a consequence, among other things, of the fact that the patient bed and the shockwave source are thus pivotable independently of one another, there is thus the initial possibility of adjusting the shockwave source and the patient bed with the patient lying thereon such relative to one another that the focal region of the shockwave source acoustically coupled to the body of the life form lies in a therapeutically relevant region as target area in the body of the patient. As a consequence of the fact that the patient bed and the shockwave source can also be synchronously pivoted around the common swiveling axis, there is subsequently the possibility of pivoting the patient bed together with the patient lying thereon around the common swiveling axis in common with the shockwave source during the treatment in the way respectively required without the focal region of the shockwaves displacing from the target area once it has been located. A renewed alignment of the shockwave source and of the patient bed with the patient lying thereon relative to one another is thus usually avoided after the pivoting event.

In an embodiment of the invention that achieves the additional object of avoiding dislocations of the therapeutically relevant region or of the target area relative to the locating means when pivoting the patient bed, a locating means is provided as a further apparatus component and is adjustable relative to the other apparatus components by being optionally pivotable around the common swiveling axis independently of the other apparatus components or synchronized with at least one of the other apparatus components. The independent pivotability of the locating means around the common swiveling axis can be utilized in order to align the apparatus components relative to one another such as required by a particular treatment case. It is thereby assured that the focal region of the shockwave source acoustically coupled to the body of the patient lies in the therapeutically relevant region that was located with the locating means. As a consequence of the fact that the locating means can be pivoted around the common swiveling axis synchronized with at least one of the other apparatus components, there is the subsequent possibility during the treatment of pivoting the patient bed together with the patient lying thereon around the common swiveling axis in the way required either in common with the shockwave source or in common with the locating means, or in common with the locating means and shockwave source without the focal region of the shockwaves being dislocated from the therapeutically relevant region once it has been located and/or without the initially located, therapeutically relevant region dislocating relative to the locating means. As was the case regarding a renewed alignment of the patient, a renewed locating of the therapeutically relevant region after the pivoting event is thus usually avoided. The common swiveling axis preferably proceeds essentially horizontally, and also proceeds roughly transversely relative to the longitudinal axis of the patient bed.

In a further modification of the invention, proceeding from a horizontal position of the patient bed, the patient bed and at least one other apparatus component are synchronously pivotable by at least 45° in at least one direction independently of the position of at least one other apparatus component relative to the patient bed. Independently of the angular position that the shockwave source and/or the locating means assume relative to the common swiveling axis with reference to the patient bed, the patient bed together with at least one of the other apparatus components can be synchronously pivoted by such an extent around the common swiveling axis so that the influence of gravity on organs and/or calculi lying in the therapeutically relevant region is considerably modified in comparison to the horizontal position of the patient bed. When a locating means is present, however, there is also the possibility—by synchronized pivoting of the patient bed together with the locating means—of first identifying the effect of gravity on the position of an organ and/or calculus lying in the therapeutically relevant region. If required, the shockwave source can be subsequently similarly pivoted around the common axis independently of the two other apparatus components. There is also the possibility of pivoting the patient bed around the common axis synchronized with the shockwave source. This permits observation of the effects produced by the pivoting with the locating means, that retains its alignment in space, and undertaking a pivot of the locating means around the common axis only when this is required. There is thus the possibility of pivoting the shockwave source and locating means by the aforementioned angle together with the patient bed.

A further modification of the inventions provides that, independently of the position that the patient bed assumes relative to the common swiveling axis, at least one of the two other apparatus components is pivotable by at least 180° relative to the patient bed. This permits the shockwave source and/or the locating means to be optionally brought into a position above or under the table independently of the angle of inclination that the patient bed assumes relative to the horizontal. When the shockwave source is in a position under the table, the shockwaves thereby act on the patient through a correspondingly shaped opening in the patient bed. The same is true when an ultrasound locating means is operated in a position under the table. When an x-ray locating means is provided, there is the possibility of optionally bringing the x-ray radiator into a position above or under the table.

In another embodiment of the invention, the locating means is spherically adjustable around an isocenter independently of the two other apparatus components and the therapeutically relevant region locatable with the locating means contains the isocenter. Alternatively, the shockwave source may be spherically adjustable around an isocenter independently of the patient bed and of the locating means, and the focal region of the shockwaves contains the isocenter. Since the patient bed together with the patient lying thereon, and the locating means or the shockwave source, are aligned such relative to one another so that the therapeutically relevant region is situated in the isocenter, the relative alignment of the locating means or of the shockwave source can be varied relative to the therapeutically relevant region lying in the isocenter without dislocations of the therapeutically relevant region relative to the locating means. It is also possible to prevent dislocations of the focal region from the therapeutically relevant region from occurring. If both the locating means as well as the shockwave source are spherically adjustable around an isocenter, it is preferable that the shockwave source and the locating means be pivotable around the same isocenter.

It is also especially advantageous if the common swiveling axis, in a further modification of the invention, proceeds through the isocenter. This is because one of the degrees of freedom required for the spherical or isocentric adjustment of the locating means or of the shockwave source is established by the pivotability of the shockwave source around the swiveling axis that is already required in the invention. This leads to a reduction in the structural outlay. The other degree of freedom required for the spherical or isocentric adjustability of the locating means or of the shockwave source is achieved with little structural outlay by the use of a C-shaped carrier pivotable around the common swiveling axis, provided at least for the locating means or for the shockwave source. The center plane of this C-shaped carrier proceeds parallel to the common swiveling axis, and the respective apparatus component is attached thereto such that it is adjustable on a circular path around the respective isocenter. One embodiment of the invention provides that the center plane of the C-shaped carrier that carries the shockwave source proceeds at a distance from the common swiveling axis, and the shockwave source is attached such to the C-shaped carrier so that its acoustic axis proceeds parallel to the center plane of the C-shaped carrier and intersects the common swiveling axis. The shockwave source is thus arranged laterally offset next to the center plane of the C-shaped carrier, so that accessibility to the patient in the region of the shockwave source is not restricted by the C-shaped carrier.

A further embodiment provides that the radii of the C-shaped carriers provided for the locating means and for the shockwave source are differently selected such that the locating means and the shockwave source can be pivoted around the common swiveling axis above one another without colliding. The collision-free adjustability of shockwave source and locating means is further promoted when, according to another embodiment of the invention, the center planes of the C-shaped carriers have different spacings from the common swiveling axis so that there is a distance between those surfaces of the C-shaped carriers facing toward one another when the C-shaped carriers are aligned parallel to one another. This insures that a suitable alignment of shockwave source and locating means can be easily found and the C-shaped carrier that carries the shockwave source does not interfere with the function of the locating means.

In another modification of the invention, the C-shaped carrier that carries the shockwave source can be pivoted into a standby position together with the shockwave source. In this standby position, the center plane of the C-shaped carrier proceeds essentially at a right angle relative to the common swiveling axis, so that the patient can be placed on the patient bed and removed therefrom without the C-shaped carrier representing an impediment.

The pivoting of the shockwave source from a position above the table into a position under the table and vice-versa is also facilitated when the shockwave source is brought into its standby position together with the C-shaped carrier for this purpose.

A further embodiment includes an x-ray diagnostics installation having an x-ray radiator and a radiation receiver, for example an x-ray image intensifier. The x-ray radiator can be used to produce an x-ray beam whose central ray proceeds through the isocenter to the radiation receiver, the x-ray radiator and the radiation receiver being attached at opposite ends of a C-arm. The C-arm is accepted in a holder displaceable such along its circumference so that the x-ray diagnostics installation is pivotable around the isocenter, and the C-arm is pivotable around the common swiveling axis. When an ultrasonic locating means, for example in the form of a sector scanner integrated in the shockwave source, is present, such a locating means then serves the purpose of acquiring additional information. The apparatus can also be operated without the additional ultrasonic locating means when the patient is transirradiated from different angles in a known way with the x-ray diagnostic means for locating the therapeutically relevant region. In a modification of the invention the center plane of the C-arm contains the common swiveling axis and that the center plane of the C-shaped carrier that carries the shockwave source proceeds at a distance from the common swiveling axis. The shockwave source is attached to the C-shaped carrier so that its acoustic axis proceeds parallel to the center plane of the C-shaped carrier and intersects the central ray of the x-ray beam in the common swiveling axis. The risk that the shockwave source or the C-shaped carrier that carries it will be situated in the beam path of the locating means is reduced to a minimum on the basis by this structure.

It is preferable that the patient bed be adjustable relative to the common swiveling axis in the directions of the axes of a three-dimensional, rectangular coordinate system. One axis of the coordinate system proceeds parallel to the longitudinal axis of the patient bed and another axis of the coordinate system proceeds parallel to the common swiveling axis. This makes it possible in a simple way to align the patient without adjusting the patient bed so that the therapeutically relevant region is situated in the isocenter, that the focal region of the shockwaves lies in the therapeutically relevant region. In a modification of the invention, the patient bed is attached to an L-shaped carrier that has one end seated pivotable around the common swiveling axis and an opposite end to which the patient bed is secured cantilevered. Good accessibility to the patient bed and to a patient lying thereon is thereby achieved.

DESCRIPTION OF THE PREFERRED EMBODIMENTS

Figure 1:
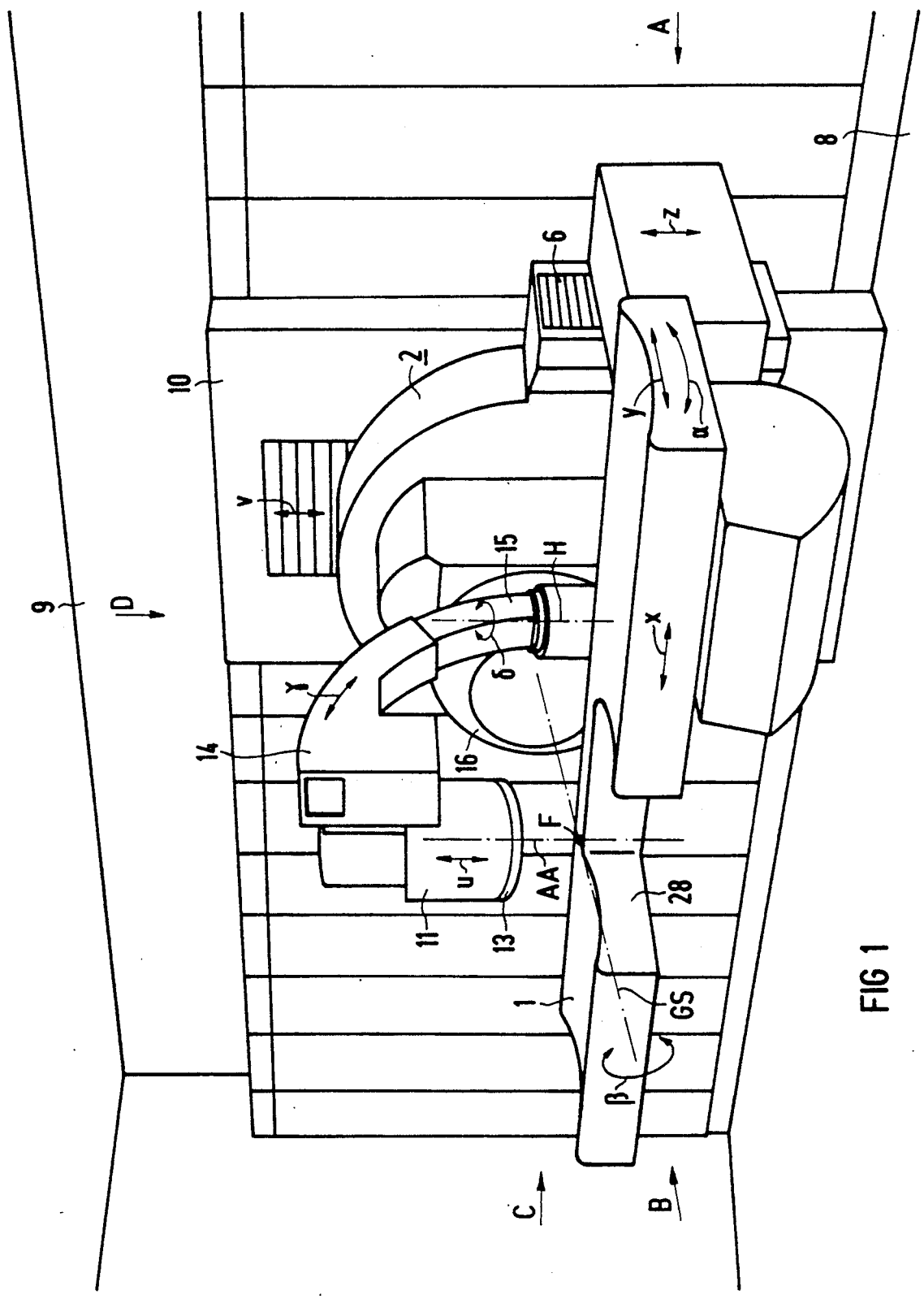
FIG. 1 is a perspective view of a medical treatment apparatus constructed in accordance with the principles of the invention.
Figure 2:
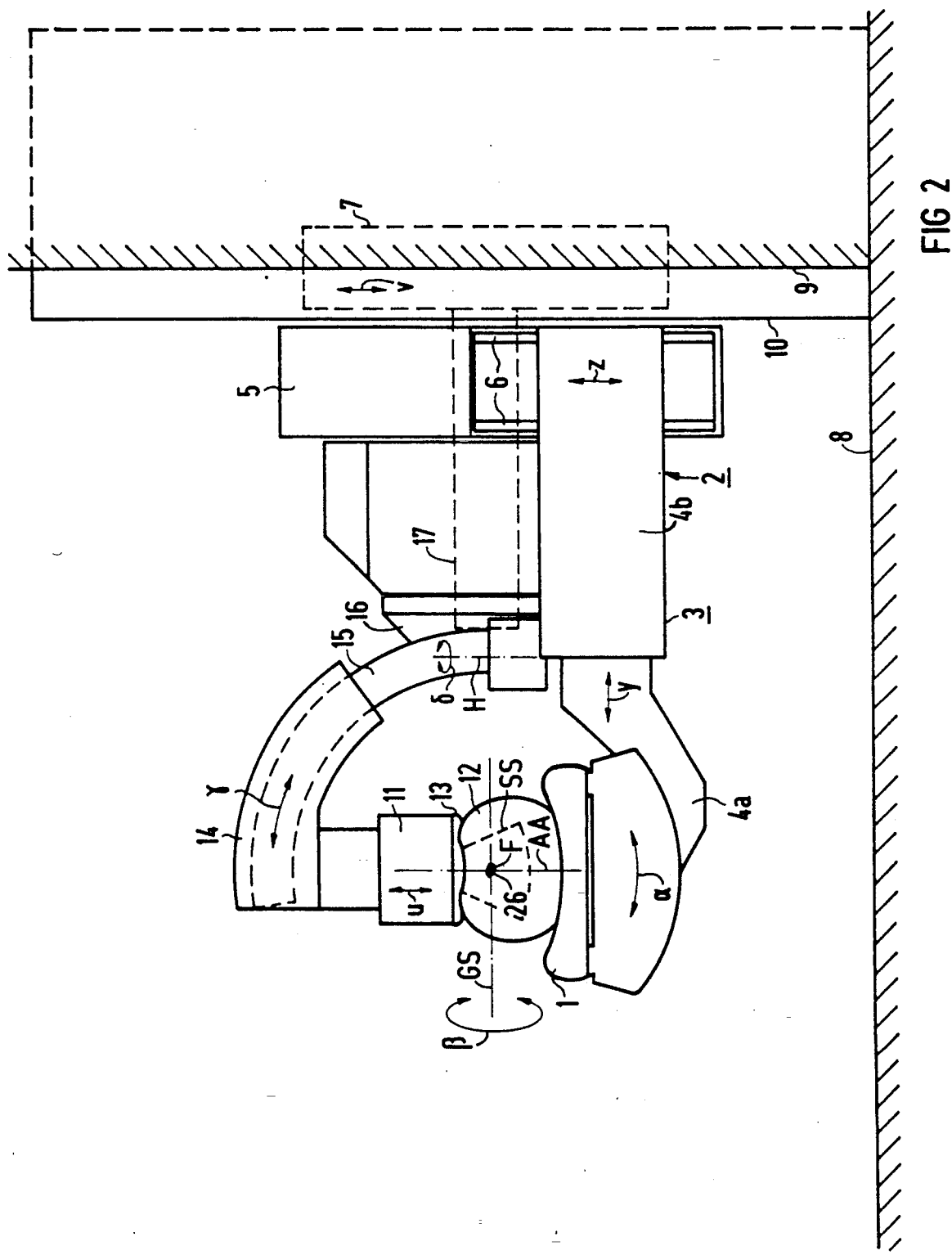
FIG. 2 is a schematic view of the apparatus of FIG. 1 in the direction of the arrow A.
Figure 3:
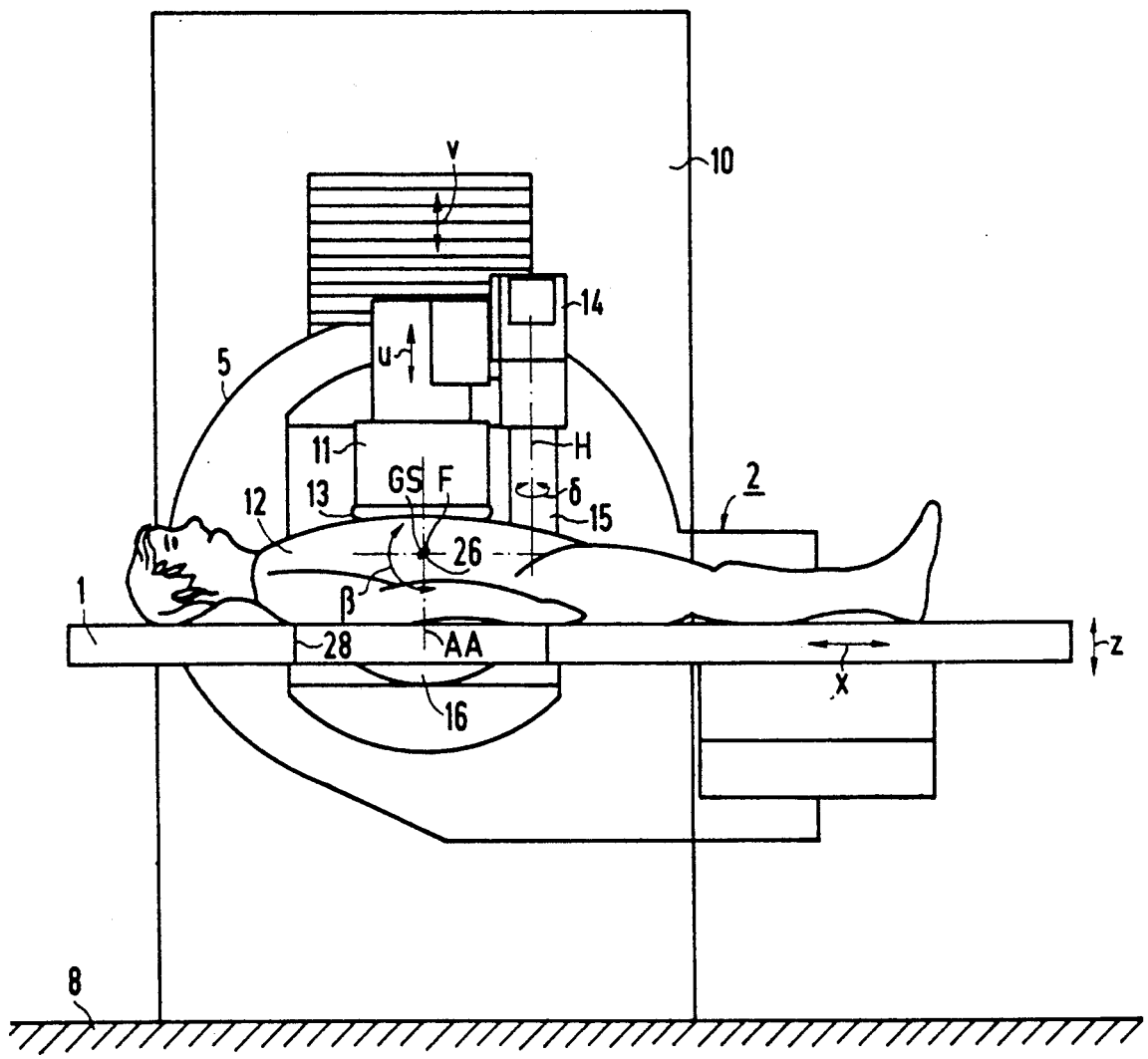
FIG. 3 is a schematic view of the apparatus of FIG. 1 in the direction of the arrow B.

As is shown in FIGS. 1 through 3, the apparatus has a patient bed 1 that is attached cantilevered to an L-shaped carrier 2 at one end; such as the foot end. The L-shaped carrier 2 has a first leg 3 having a free end to which the patient bed 1 is secured. The first leg 3 has two approximately box-shaped leg sections 4a and 4b each having a rectangular cross-section. Upon interposition of a guide (not shown), the sections 4a and 4b are inserted into one another in telescoping fashion so that the patient bed 1 secured to the leg section 4a is adjustable on a straight line transversely relative to the direction of its longitudinal axis in the direction of the double arrow y. The patient bed 1 is secured to the free end of the L-shaped carrier (i.e. of the leg section 4a) with suitable guide means (not shown) so that it is adjustable on a straight line in the direction of its longitudinal axis, i.e. in the direction of the double arrow x. Further, the patient bed 1 is also secured to the free end of the first leg 3 with suitable articulation means (likewise not shown) so that it can be tilted in the direction of the curved double arrow α around an axis proceeding above the patient bed and parallel to the longitudinal axis thereof.

Via a suitable guide 6 indicated in FIG. 2, leg section 4b, of the first leg 3 is a substantially circular disk-shaped second leg 5 of the L-shaped carrier 2 so as to be adjustable on a straight line in the direction of the double arrow z. Thus the patient bed is adjustable in a direction that proceeds at a right angle relative to the plane thereof. The second leg 5 of the L-shaped carrier 2 is attached to a carriage 7 indicated in FIG. 2 which by a suitable guide (not shown), is in turn attached to a stand 10 that stands on the floor 8 of the examination room and is set into the wall thereof. The second leg 5 and the assembly attached thereto are thus adjustable on a straight line in the direction of the double arrow v, i.e. in the vertical direction.

The apparatus also includes a schematically indicated shockwave source 11 with which focused shockwaves can be generated. The shockwave source includes suitable means for converging the shockwaves in a focal region F that lies on the acoustic axis AA of the shockwave source 11. The shockwave source 11, for example, may be an electro-dynamic shockwave source as disclosed in German published application No. 33 28 051 or corresponding U.S. Pat. No. 4,674,505 which is incorporated herewith by reference. The shockwave source 11 contains an ultrasound locating means (not shown in FIGS. 1 through 3) which includes at least one ultrasound sector scanner with which a circular-sector-shaped slice SS of the body of the patient 12, that contains the acoustic axis AA and the focal region F and that is indicated in FIG. 2, can be scanned. A shockwave source having integrated ultrasound locating means is disclosed in German published application No. 37 25 533, corresponding to U.S. Pat. No. 4,928,672. The shockwave source 11 has a space closed with a flexible bellows 13 and filled with an acoustic propagation medium for the shockwaves, for example water, and is acoustically coupled to the body of the patient 12 by pressing the bellows 13 against the body surface of the patient, as shown in FIG. 2.

The shockwave source 11 is attached to a carriage 14 that is guided with a suitable guide (not shown) on a C-shaped carrier 15 having a roughly quadratic cross-section that is curved in the shape of a circular arc. The carriage 14 that carries the shockwave source 11 is adjustable in the direction of the curved double arrow "γ" along the circumference of the C-shaped carrier 15 that extends over approximately 90°. During normal operation of the apparatus, the focal region F of the shockwaves lies on the middle axis of the C-shaped carrier 15. The shockwave source 11, whose acoustic axis AA intersects the center axis of the C-shaped carrier 15 at a right angle, is thus pivotable in such a way on a circular orbit around the center axis of the C-shaped carrier 15 that the focal region F of the shockwaves always lies on the center axis of the C-shaped carrier 15 and the acoustic axis AA always lies in a plane that contains the center axis of the C-shaped carrier 15. The shockwave source 11 is attached to the carriage 14 so that its acoustic axis AA proceeds laterally offset at a distance from the center plane of the C-shaped carrier 15 and parallel thereto. Via a guide (not shown), the shockwave source 11 is attached displaceable on a straight line in the direction of the double arrow u parallel to its acoustic axis AA, whereby the focal region F of the shockwaves lies on the center axis of the C-shaped carrier 15 in the radially innermost position of the shockwave source 11.

The laterally offset mounting of the shockwave source 11 at the carriage 14 results in the accessibility to that region of the body of the patient 12 to which the shockwave source 11 is coupled not being restricted by the C-shaped carrier 15. A repositioning of a patient 12 lying on the patient bed 1 is facilitated when the shockwave source 11 is moved into its radially outermost position in the direction of the double arrow u.

The C-shaped carrier 15 is connected to a carrying part 16 that, as the second leg 5 of the L-shaped carrier 2, is attached to the carriage 7 that is attached to the stand 10 adjustable on a straight line in the direction of the double arrow v. The patient bed 1 and the shockwave source 11 are thus adjustable in common in the direction of the double arrow v by displacing the carriage 7 at the stand 10.

In addition to the adjustment possibilities already set forth, the shockwave source 11 as well as the patient bed 1 are pivotable around a common swiveling axis GS that proceeds substantially horizontally, and substantially transversely relative to the longitudinal axis of the patient bed 1. This common swiveling axis GS proceeds through the focal region F of the shockwaves during normal operation of the apparatus, i.e. when the shockwave source 11 assumes its radially innermost position. This is achieved by a shaft 17, indicated with broken lines in FIG. 2, attached to the carriage 7. The second leg 5 of the L-shaped carrier 2 that carries the patient bed 1, and the carrying part 16 that carries the C-shaped carrier 15 with the shockwave source 11, are attached to the shaft 17 so as to be pivotable in the direction of the curved double arrow β (not shown in detail). The C-shaped carrier 15 is attached to the carrying part 16 eccentrically offset by the required dimension with reference to the common swiveling axis GS in order that the acoustic axis AA of the shockwave source 11 (which, as described, proceeds at a distance from the center plane of the C-shaped carrier 15 and parallel thereto) intersects the common swiveling axis GS. During normal operation of the apparatus, the C-shaped carrier 15 assumes a position such that its center plane proceeds parallel to the common swiveling axis GS.

As a consequence of the described pivotability of the C-shaped carrier 15 together with the shockwave source 11 around the common swiveling axis, as well as a consequence of the described adjustability of the shockwave source 11 along the circumference of the C-shaped carrier 15 on a circular path, the shockwave source 11 is spherically adjustable around the focal region F that forms an isocenter lying on the common swiveling axis GS. An isocentric adjustability of the shockwave source 11 shall therefore be referred to below.

Figure 4:
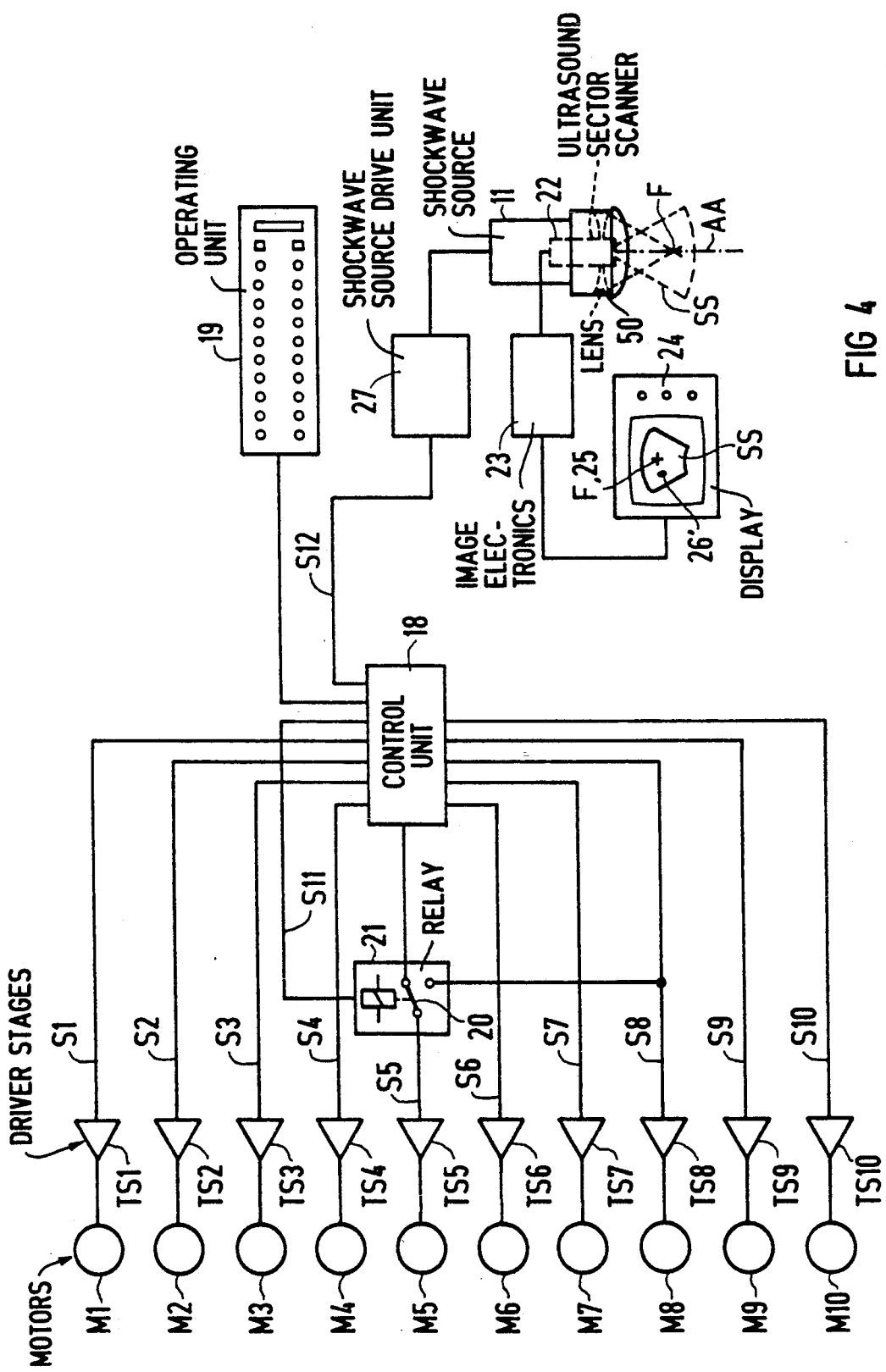
FIG. 4 is a schematic block circuit diagram of the apparatus of the invention.

In order to be able to execute the described adjustment motions, motors M1 through M10 (not shown in FIGS. 1 through 3) are present, which respectively operate on the part to be adjusted via suitable gears (not shown). The motors M1 through M10 are schematically indicated in FIG. 4. The motor M1 serves the purpose of adjusting the patient bed in the direction of the double arrow x. The motor M2 serves the purpose of adjusting the leg section 4a of the first leg 3 together with the patient bed 1 in the direction of the double arrow y. The motor M3 serves the purpose of adjusting the first leg 3 together with the patient bed 1 in the direction of the double arrow z. The motor M4 serves the purpose of tilting the patient bed 1 in the direction of the curved double arrow α and the motor M5 serves the purpose of pivoting the L-shaped carrier 2 together with the patient bed 1 around the common swiveling axis GS in the direction of the curved double arrow β.

The motor M6 adjusts the carriage 7 and, thus the patient bed 1 and the shockwave source 11, in the direction of the double arrow v.

The motor M7 serves the purpose of adjusting the carriage 14 together with the shockwave source 11 in the direction of the curved double arrow "γ". The motor M8 effects the adjustment of the shockwave source 11 in the direction of the double arrow u. The motor M1 serves the purpose of pivoting the carrying part 16 together with the C-shaped carrier 15 and the shockwave source 11 around the common swiveling axis GS in the direction of the curved double arrow β.

The purpose of the motor M10 that is also shown in FIG. 4 shall be set forth later.

Via schematically indicated driver circuits TS1 through TS10, the motors M1 through M10 are connected via control lines S1 through S10 to a control unit 18 to which an operating unit 19 is connected. The operating unit 19 has two keys for each of the motors M1 through M10, one of these keys causing the respective motor to run in the forward direction as long as it is pressed and the other key causing the respective motor to run in the reverse direction as long as it is pressed. The motors M5 and M8 and the corresponding gearings are selected such that the adjustment of the patient bed 1 or of the shockwave source 11 in the direction of the curved double arrow β respectively ensue with exactly the same angular speed. The switchover contact 20 of a relay 21, whose excitation coil is connected via a control line S11 to the control unit 18 lies in the control line S5 that leads from the control unit 18, to the driver stage TS5 that belongs to the motor M5. In the normal case, the switch-over contact 20 assumes the switch position shown in FIG. 4. The operating unit 19 has two additional keys that are distinguished from the keys allocated to the motors M1 through M10 by having a different shape. When one of these additional keys is actuated, the relay 21 is driven by the control unit 18 via the control line S11 such that the switch status of the switch-over contact 20 changes. The driver stage TS5 belonging to the motor M5 is then connected to the control line S8 leading to the driver stage TS8 that belongs to the motor M8. This control line S8-dependent on which of the two additional keys is pressed-carries a control signal that effects a rotation of the motors M5 and M8 in the one or in the other direction. As long as one of the two additional keys is pressed, the motors M5 and M8 that serve the purpose of pivoting the patient bed 1 or the shockwave source 11 are thus activated in common such that the patient bed 1 and the shockwave source 11 are synchronously pivoted around the common swiveling axis GS in the one or in the other direction in the direction of the curved double arrow β. Thus the patient bed 1 and the shockwave source 11 are optionally pivotable around the common swiveling axis GS independently of one another or synchronously. For reasons that shall be set forth later, it is thereby expedient that the patient bed 1 and the shockwave source 11—regardless of the position that the shockwave source 11 assumes relative to the patient bed 1—be pivoted synchronized by at least 45° in at least one direction proceeding from the horizontal position of the patient bed 1 shown in FIGS. 1 through 3. In the described exemplary embodiment, a synchronous pivotability of 90° is provided in both directions.

In FIG. 4, the shockwave source 11 is also indicated as having an acoustic converging lens 50 as means for converging the shockwaves and an ultrasound sector scanner 22 integrated therein. Via a known image generating and control electronics 23, the ultrasound sector scanner 22 is connected to monitor 24 that serves the purpose of portraying the slice SS of the body of the patient 12 that is scanned with the ultrasound sector scanner 22 and contains the focal region F. The position of the focal region F is identified by a mark 25 mixed into the monitor picture with the image generating and control electronics 23. The image 26' of a calculus to be disintegrated that is indicated at 26 in FIG. 2 is also indicated in the monitor picture in FIG. 4.

FIG. 4 also indicates a generator circuit 27 connected to the shockwave source 11, this generator circuit 27 serving the purpose of driving the shockwave source 11 to generate shockwaves. The generator circuit 27 is connected to the control unit 18 via a control line S12. When a key of the operating unit 19, that differs from the other keys on the basis of its shape and size, is actuated, the control unit 18 initiates the generator circuit 27 to drive the shockwave source 11 to output a preselectable plurality of successive shockwaves.

In order to disintegrate a calculus 26, for example a kidney stone or a gall stone, in the body of a patient 12, one proceeds, for example, by first bringing the patient bed 1 into a horizontal position, and into its lowest position by adjusting the carriage 7. Subsequently, the shockwave source 11 is moved into its radially outermost position in the direction of the double arrow u. The patient 12 is then placed on the patient bed 1, such that the target area, i.e. the organ that has the calculus 26, is situated approximately under the shockwave source 11. It can thereby be expedient to tilt the patient bed 1 in the one or other directions of the curved double arrow "alpha" so that, as a consequence of the force of gravity, the calculus 26 to be disintegrated assumes a stable position in the respective organ. Following thereupon, the patient bed 1 is brought to a height that is comfortable for the attending physician, by adjusting the carriage 7. Moreover, the shockwave source 11 is adjusted to its radially innermost position in the direction of the double arrow u so that the focal region F lies on the common swiveling axis GS. The flexible bellows 13 of the shockwave source 11 is pressed against the body surface of the patient 12, that was previously coated with an ultrasound gel or the like in order to improve the acoustic coupling. The patient bed 1 is now displaced back and forth in the direction of the double arrow x until the calculus 26 to be disintegrated lies in the slice SS scanned with the ultrasound sector scanner 22 and, consequently, the image 26' of the calculus 26 is visible on the monitor 24. The ultrasound sector scanner 22 is preferably aligned such that the scanned slice SS contains the common swiveling axis GS. If case the patient 12 was placed on the patient bed 1 in an unfavorable position at the beginning, it may be necessary to additionally adjust the patient bed 1 in the direction of the double arrows z and/or y so that the calculus 26 to be disintegrated can be brought into the slice SS that can be scanned with the ultrasound sector scanner 22. When the image 26' of the calculus 26 to be disintegrated appears on the monitor 24, the patient 12 is positioned by adjusting the patient bed 1 in the direction of the double arrows y and/or z that the image 26' of the calculus 26 to be disintegrated coincides in the picture of the monitor 24 with the mark 25 that corresponds to the position of the focal region F. Proceeding from this position, there is then the possibility—by adjusting the carriage 14 in the direction of the double arrow "γ" and/or by pivoting the C-shaped carrier 15 around the common swiveling axis GS in the direction of the curved double arrow β—of aligning the shockwave source 11 relative to the patient 12 such that neither impediments such as bones, nor organs such as the lung that could be damaged by the action of the shockwaves are situated in the propagation path of the shockwaves. As a consequence of the fact that the shockwave source 11 is isocentrically adjusted around the focal region F, there is thus no risk that the focal region F will dislocate such that it comes to lie outside of the calculus 26 to be disintegrated. When the optimal alignment of the shockwave source 11 has been found, the shockwave treatment can be started. When required, a synchronous pivoting of the patient bed 1 and of the shockwave source 11 can ensue around the common swiveling axis GS in the direction of the curved double arrow β before or during the treatment in order to stabilize the position of a calculus to be disintegrated with the force of gravity. No dislocations of the focus F occur. It might at most be necessary to slightly correct the alignment of the patient 12 relative to the shockwave source 11 by adjusting the patient bed 1 to take a potential change in the position of the calculus 26 into consideration. Particularly given pivoted positions that greatly deviate from the horizontal (as a consequence of the synchronous pivotability of the patient bed 1 together with the shockwave source 11 by ±90° around the common swiveling axis GS, the patient 12 can, for example, be brought into a standing position) it is expedient before the pivoting of the patient bed 1 around the common swiveling axis GS to attach a footrest to the patient bed 1 and to fix the patient 12 with belts or the like.

After the end of the treatment, the patient bed is again lowered as needed in order to be brought into its horizontal initial position and the shockwave source 11 is adjusted into its radially outermost position so as to be able to take the patient comfortably from the patient bed 1.

Figure 7:
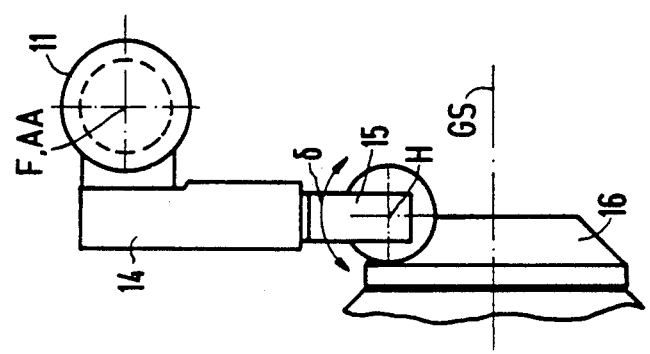
FIG. 7 shows a schematic, partial view in the direction of the arrow D in FIG. 1 without patient bed that illustrates a further operating condition of the apparatus.

For specific treatment cases, preferably when disintegrating kidney stones of a patient 12 lying on his back on the patient bed 1, it is necessary to be able to bring the shockwave source 11, shown in its position above the table in FIGS. 1 through 3, into a position under the table in which it is acoustically coupled to the body of a patient lying on the patient bed 1 through an opening 28 shown in FIG. 1. The opening 28 can be closed with a suitably shaped closure member (not shown) for operation of the apparatus with the shockwave source 11 situated above the table. To this end, the C-shaped carrier 15 that carries the shockwave source 11—independently of the respective pivoted position that the patient bed assumes relative to the common swiveling axis GS in the direction of the curved double arrow β—can be pivoted by at least 180° into the position shown in FIGS. 5 and 6, wherein the position of the shockwave source 11 of FIGS. 1 through 3 is indicated with broken lines. For this purpose, the C-shaped carrier 15 is attached to the carrying part 16 so as to be pivotable in the direction of the curved double arrow δ around an axis H disposed in a plane that proceeds perpendicularly relative to the common swiveling axis GS. The attachment is such that the C-shaped carrier 15 together with the shockwave source 11 as shown in FIG. 7 can be pivoted into a standby position wherein the center plane of the C-shaped carrier 15 proceeds at approximately a right angle relative to the common swiveling axis GS. If the patient bed 1 is now brought in the direction of the double arrow y into its position farthest from the stand 10, the shockwave source 11 situated in its standby position can be pivoted collision-free from its above-table position into its below-table position at the patient bed 1 and vice-versa. To prevent the shockwave source 11 or the C-shaped carrier 15 from touching the floor, the patient bed 1 is brought to a height, by adjusting the carriage 7, such that an adequate clearance from the floor is present. The shockwave source 11 must be pivoted out of its standby position for the operation of the apparatus. Moreover, the shockwave source 11 can also be brought into its standby position to facilitate the placement of a patient 12 onto the patient bed 1 or the removal of the patient 12 from the patient bed 1. When the shockwave source 11 assumes its under-table position the adjustability of the patient bed 1 in the direction of the double arrows x and y is limited by the dimensions of the opening 28.

In the described exemplary embodiment, the shockwave source 11 is spherically adjustable around the focal region F as an isocenter lying on the common swiveling axis GS. The described, synchronous pivoting of patient bed 1 and shockwave source 11 around the common swiveling axis GS, however, is also possible without dislocation of the focal region F if it is not an isocentric, in which case some other adjustability of the shockwave source 11 relative to the patient bed 1 is established when the focal region F does not lie on the common swiveling axis GS.

The apparatus of the invention shown in FIGS. 8 through 11 has structure in common with the embodiments set forth above, for which identical parts bear the respectively same reference characters. The main difference in the embodiment of FIGS. 8 through 11 from the exemplary embodiments set forth above is that the apparatus of FIGS. 8 through 11—in addition to including the ultrasound sector scanner 22—has an x-ray diagnostics installation referenced 29 in general, as a further locating means. This includes an x-ray radiator 30, an x-ray image intensifier 31 and a C-arm 32 that embraces the patient bed 1 that is transmissive for x-rays in the region of its seating surface for the patient. The x-ray radiator 30 can be used to generate an x-ray beam whose central ray ZS proceeds centrally through the input luminescent screen of the x-ray image intensifier 31. The C-arm 32 extends over approximately 180° and the x-ray radiator 30 and the x-ray image intensifier 31 are attached at opposite the ends of the C-arm 32 so that central ray ZS of the x-ray beam proceeds in the center plane of the C-arm 32 and intersects its center axis at a right angle. With suitable guide means (not shown), the C-arm 32 is adjustably accepted in a holder 33 so that it is pivotable along its circumference around a center axis in the direction of the curved double arrow ε. The x-ray radiator 30 and the image intensifier 31 are thereby pivoted on a circular path around the center axis of the C-arm 32, whereby the central ray ZS of the x-ray beam always intersects the center axis of the C-arm 32. With suitable guide means (not shown), the x-ray image intensifier 31 is attached to the C-arm 32 so that it is displaceable on a straight line in the direction of the double arrow w parallel to the central ray ZS of the x-ray beam. It is thus possible to position the x-ray image intensifier 31 optimally close to the body surface of a patient 12 lying on the patient bed 1.

Just as the second leg 5 of the L-shaped carrier 2, the carrying part 16 connected to the C-shaped carrier 15 and the holder 33 that accepts the C-bend 32 are attached to the carriage 7 that is adjustable on a straight line in the direction of the double arrow v at the stand 10. The patient bed 1, the shockwave source 11 and the x-ray diagnostics installation 29 are thus adjustable in common in the direction of the double arrow v by displacing the carriage 7 at the stand 10.

The adjustment possibilities present in the exemplary embodiment set forth above are established for the patient bed 1 as well as for the shockwave source 11, i.e. these two apparatus components are pivotable, among other things, around the common swiveling axis GS. During normal operation of the apparatus, i.e. when the shockwave source 11 assumes its radially innermost position, this common swiveling axis GS again proceeds through the focal region F of the shockwaves and also intersects the central ray ZS of the x-ray beam, which in turn proceeds through the focal region F of the shockwaves. The x-ray diagnostics installation 29 is also pivotable around the common swiveling axis GS. This is achieved in that (in addition to the second leg 5 of the L-shaped carrier 2 that carries the patient bed 1) the holder 33 that accepts the C-arm 32 is seated on the shaft 17 (shown with broken lines in FIG. 9) so as to be pivotable, in way not shown in greater detail, in the direction of the curved double arrow β. The carrying part 16 that carries the C-shaped carrier 15 with the shockwave source 11 is seated (in a way not shown in detail) at the holder 33 pivotable around the common swiveling axis GS in the direction of the curved double arrow β. Since the center plane of the C-arm 32 contains the common swiveling axis GS, and the center axis of the C-arm 32 intersects the common swiveling axis GS, it is assured that the central ray ZS of the x-ray beam during normal operation always proceeds, as stated, through the focal region F of the shockwaves.

As stated above, the C-arm 32 together with the x-ray diagnostics installation 29 is pivotable around the common swiveling axis GS that proceeds through the focal region F of the shockwaves, and of the x-ray diagnostics installation 29 together with the C-arm 32 is adjustable on a circular path around the middle axis of the C-bend 32 that proceeds through the focal region F of the shockwaves. This means that not only the shockwave source 11, but also the x-ray diagnostics installation 29, is spherically adjustable around the focal region F of the shockwaves that forms the isocenter lying on the common swiveling axis GS. An isocentric adjustability of the x-ray diagnostics installation 29 shall therefore also be referred to below.

Figure 10:
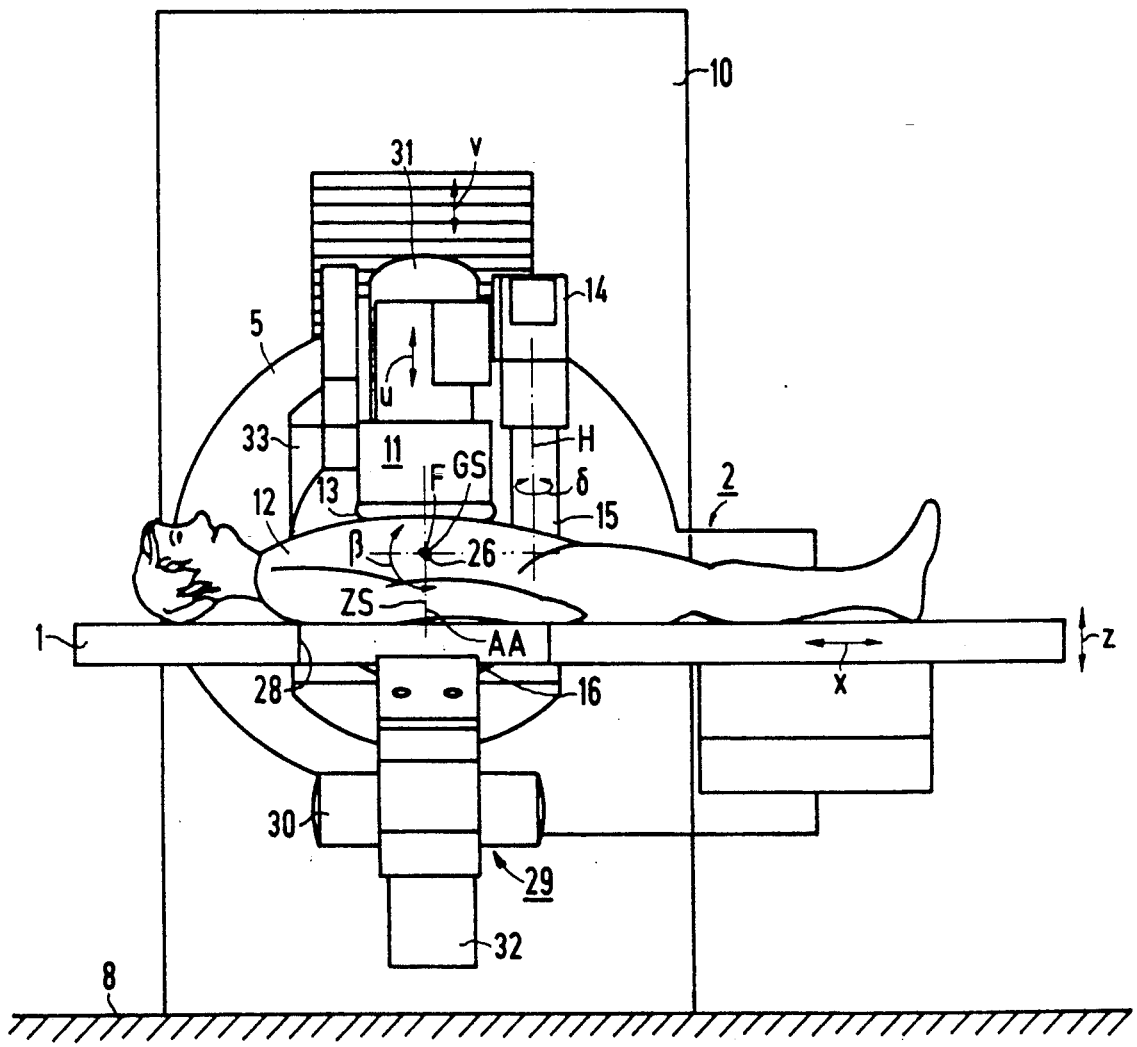
Figure 11:
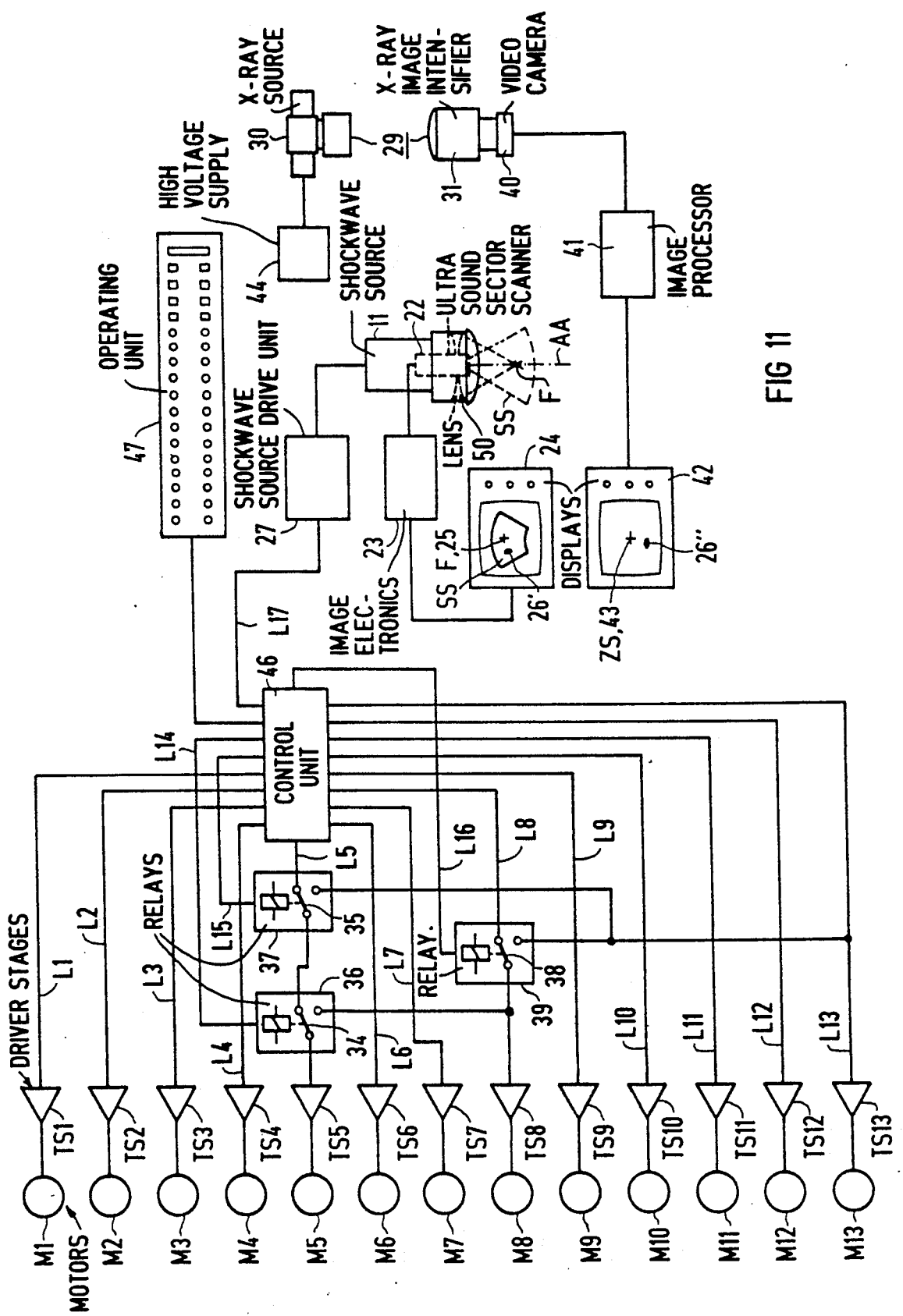

To be able to execute the described adjustment motions, motors M1 through M13 that are (not shown in FIGS. 8 through 10) are provided. These act on the part to be respectively adjusted via suitable gearings (not shown). The motors M1 through M13 are schematically indicated in FIG. 11. The motors M1 through M10 thereby serve the purposes already set forth in conjunction with the earlier-described exemplary embodiment.

The motor M11 serves the purpose of adjusting the x-ray image intensifier 31 of the x-ray diagnostics installation 29 in the direction of the double arrow w; the motor 12 effects pivoting of the x-ray diagnostics installation 29 in the direction of the curved double arrow ε, and the motor 13 serves the purpose of pivoting the holder 33 with the x-ray diagnostics installation 29 around the common swiveling axis GS in the direction of the curved double arrow β.

Via schematically indicated driver circuits TS1 through TS13, the motors M1 through M13 are connected via control lines L1 through L13 to a control unit 46 to which an operating unit 47 is connected. The operating unit 47 has two keys for each of the motors M1 through M13, one of which causes the respective motor to run in the forward direction as long as it is pressed and the other of which causes the respective motor to run in the reverse direction as long as it is pressed. The motors M5, M8 and M13 and the corresponding gearings are selected such that the adjustment of the patient bed 1, the shockwave source 11 and the x-ray diagnostics installation 29 in the direction of the curved double arrow β respectively exactly ensues with the same angular speed. The switch-over contacts 34 and 35 of two relays 36 and 37 are in series in the control line L5 that leads from the control unit 46 to the driver stage TS5 that belongs to the motor M5. The switch-over contact 38 of a relay 39 lies in the control line L8 that leads from the control unit 46 to the driver stage TS8 that belongs to the motor M8. In the normal case, the switch-over contacts 34, 35 and 38 of the relays 36, 37 and 39, whose excitation coils are connected via control lines L14, L15 and L16 to the control unit 46, assume the switch position shown in FIG. 4, so that the motors M5, M8 and M13 can be activated independently of one another by actuating the corresponding keys of the operating unit 47. The operating unit 47, however, has four additional key pairs whose keys differ from the keys allocated to the motors M1 through M13 by having a different shape. When one of the keys of the first additional key pair is pressed, the switch-over contact 34 of the relay 36 changes its switch position as long as the key is pressed, so that the driver stage TS5 is connected to the control line L8 leading to the driver stage TS8. This control line L8 carries a control signal—dependent on which of the two additional keys is pressed—that allows the motors M5 and M8 to rotate in common in the one or in the other direction. As long as a key of the first additional key pair is pressed, thus, the patient bed 1 and the shockwave source 11 are synchronously pivoted in the one or in the other direction around the common swiveling axis GS in the direction of the curved double arrow β, dependent upon which of the keys of the first additional key pair is activated. In a corresponding fashion, the switch position of the switch-over contact 35 of the relay 37 is changed upon actuation of one of the keys of the second additional key pair, so that the driver stage TS5 is connected to the control line L13 that leads to the driver stage TS13. This control line L13—dependent on which of the two additional keys is pressed—carries a control signal that effects a common rotation of the motors M5 and M13 in one or the other direction. Dependent upon which of the two keys of the second additional key pair is actuated, thus, the patient bed 1 and the x-ray diagnostics installation 29 are pivoted in one or the other direction around the common swiveling axis GS in the direction of the curved double arrow $\beta$. In a corresponding fashion, the switch position of the switch-over contact 38 of the relay 39 changes given actuation of one of the keys of the third additional key pair, so that the driver stage TS8 is connected to the control line L13 that leads to the driver stage TS13. This control line 13—dependent on which of the two additional keys is pressed—carries a control signal that initiates a common rotation of the motors M8 and M13 in one or the other direction. Dependent upon which of the two keys of the third additional key pair is actuated, thus, the shockwave source 11 and the x-ray diagnostics installation 29 are synchronously pivoted around the common swiveling axis GS in one or the other direction in the direction of the curved double arrow $\beta$. When, finally, one of the keys of the fourth additional key pair is actuated, the switch-over contact 35 as well as the switch-over contact 38 change their respective switch positions, so that the driver stages TS5 and TS8 are connected to the control line L13 that leads to the driver stage TS13. This control line L13—dependent upon which of the two additional keys is pressed—carries a control signal that effects a common rotation of the motors M5, M8 and M13 in one or the other direction. A common, synchronized pivoting of the patient bed 1, the shockwave source 11 and the x-ray diagnostics installation 29 then ensues around the common swiveling axis GS in the direction of the curved double arrow $\beta$.

Figure 8:
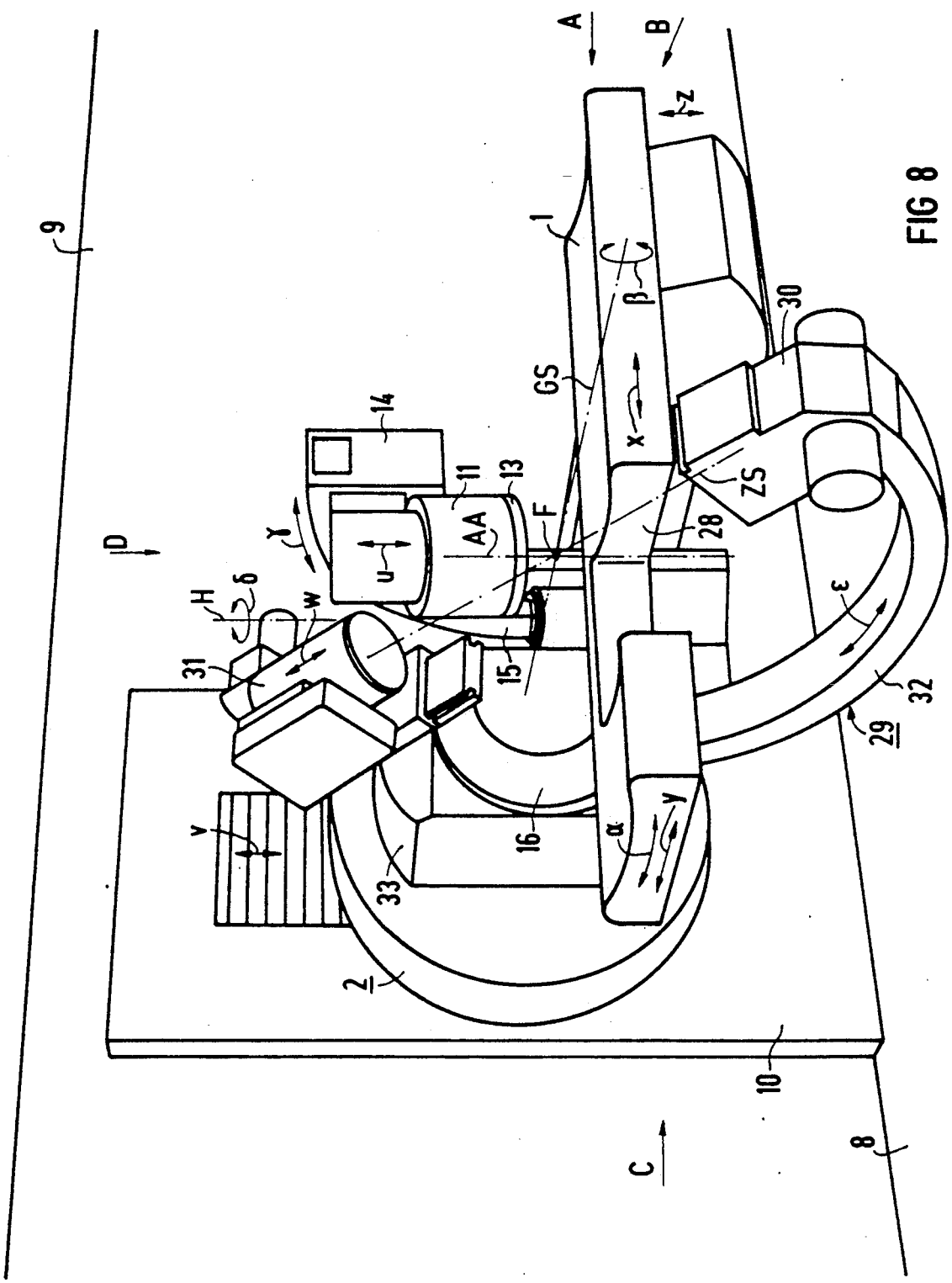
FIGS. 8 through 11 show a further embodiment of an apparatus of the invention in illustrations analogous to those of FIGS. 1 through 4.
Figure 9:
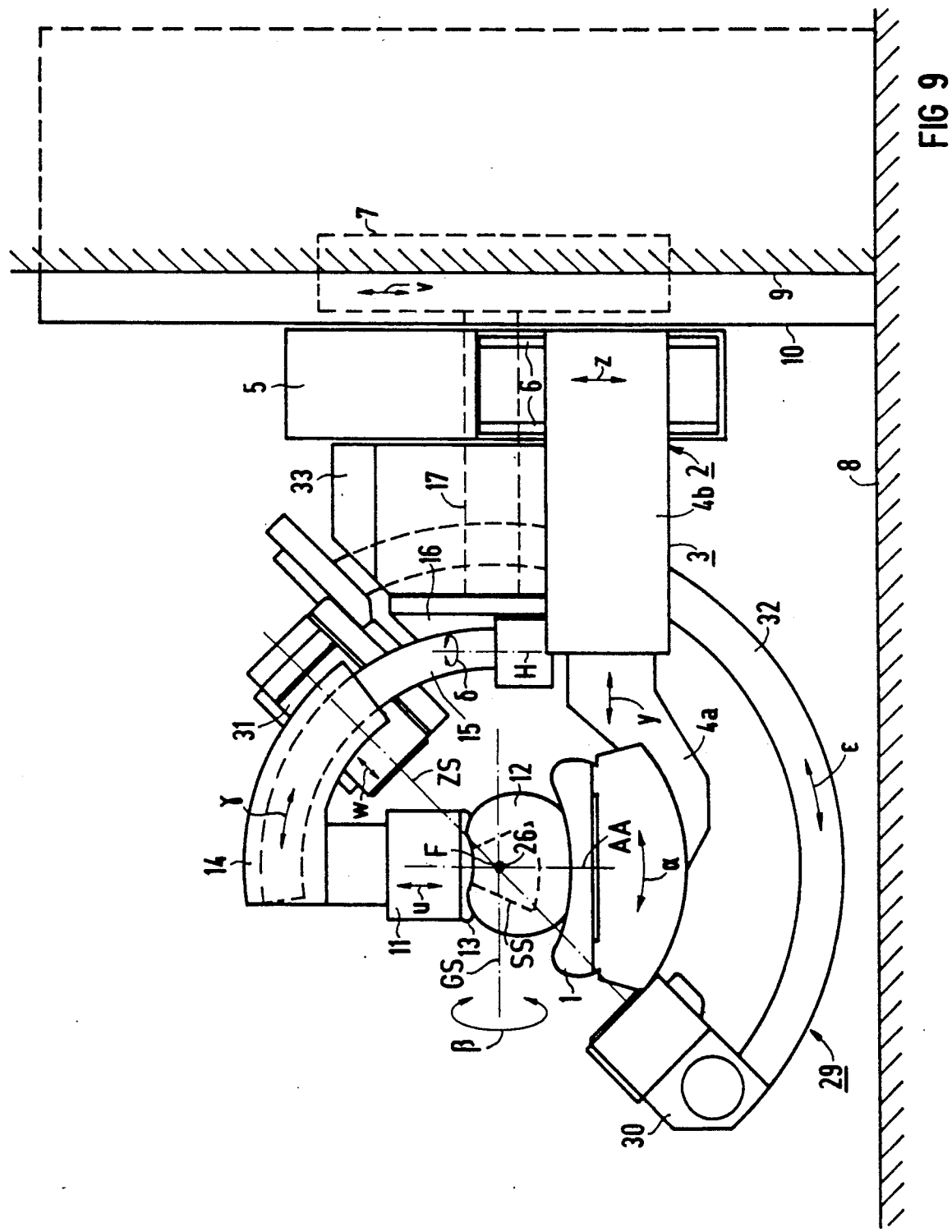

Thus the patient bed 1, the shockwave source 11 and the x-ray diagnostics installation 29 are optionally pivotable around the common swiveling axis GS in one or the other direction identified by the curved double arrow $\beta$ independently of one another, or two of these apparatus components are synchronously pivotable therearound in common, or all three apparatus components are synchronously pivotable therearound in common. For reasons set forth below, it is preferable that the shockwave source 11 and/or the x-ray diagnostics installation 29—regardless of the position that the shockwave source 11 and/or the x-ray diagnostics installation 29 assumes relative to the patient bed 1—be synchronously pivotable in common with the patient bed 1 by at least 45° in at least one direction proceeding from the position of the patient bed 1 that is shown in FIGS. 8 through 10, and that is horizontal with reference to the common swiveling axis GS. A synchronous pivotability of 90° in both directions is provided in the case of the described exemplary embodiment.

FIG. 11 also again shows the shockwave source 11 having an acoustic lens 50 and an ultrasound sector scanner 22 integrated therein, the image generating and control electronics 23 and the monitor 24. Further, FIG. 11 again indicates the generator circuit 27 connected to the shockwave source 11. The generator circuit 27 is connected to the control unit 46 via a control line L17. When a key of the operating unit 47, that differs from the other keys on the basis of its shape and size, is actuated, the control unit 46 enables the generator circuit 27 to drive the shockwave source 11 to output a preselectable plurality of successive shockwaves.

FIG. 11 also schematically indicates the x-ray radiator 30 and the x-ray image intensifier 31 of the x-ray diagnostics installation 29. A schematically indicated video camera 40 is connected to the x-ray image intensifier 31. The video camera 40 records the image of the output luminescent screen of the x-ray image intensifier 31 and converts it into a video signal that is supplied to an image processor. The signal then proceeds to a further monitor 42 that serves the purpose of portraying the x-ray image acquired with the x-ray diagnostics installation 29. A mark 43 that identifies the position of the central ray ZS of the x-ray beam is mixed into the monitor picture by the image processor 41. The x-ray radiator 30 is connected to a high-voltage 44 that supplies the voltages that are required for the operation of the x-ray radiator 30.

To disintegrate a calculus 26, for example a kidney stone or a gall stone in the body of a patient 12, a procedure similar to that set forth in conjunction with the first-described exemplary embodiment is undertaken. In the embodiment of FIGS. 8-11, however, the x-ray diagnostics installation 29 is aligned, before the shockwave source 11 is brought into its radially innermost position such that the image 26" of the calculus 26 to be disintegrated is highly visible in the video picture portrayed on the monitor 42. Subsequently, the patient 12 is aligned, by adjusting the patient bed 1 in the direction of the double arrows x and/or y, so that the image 26" of the calculus 26 to be disintegrated is situated at least in the proximity of the mark 43. Only now is the shockwave source 11 adjusted in the direction of arrow u into its radially innermost position, wherein the focal region F lies on the common swiveling axis GS and on the central ray ZS of the x-ray beam. The patient 12 is then positioned in the way already set forth above so that the image 26' of the calculus 26 to be disintegrated coincides with the mark 25 in the picture of the monitor 24 that corresponds to the position of the focal region F. When this setting has been found, the image 26" of the calculus 26 to be disintegrated also coincides with the mark 43 on the monitor 42. Proceeding from the position that has thus been found, there is then the possibility of aligning the shockwave source 11 in the desired way by adjustment around the focal region F as isocenter. If necessary, the x-ray diagnostics installation 29 can be synchronously pivoted with the shockwave source 11 around the common swiveling axis GS in the direction of the curved double arrow $\beta$ and/or the alignment of the x-ray diagnostics installation 29 can be adapted in some other way to the modified alignment of the shockwave source 11. As a consequence of the fact that not only is the shockwave source 11 but also the x-ray diagnostics installation 29, isocentrically adjusted relative to the focal region F, there is no risk whatsoever that the focal region F will dislocate so that it comes to lie outside of the calculus 26 to be disintegrated, or that the x-ray diagnostics installation 29 assumes such a position that the central ray ZS of the x-ray beam does not proceed through the focal region F. Under certain circumstances the shockwave source 11 and the x-ray diagnostics installation 29 may be aligned relative to one another such that an imaging of the shockwave source 11 in the x-ray image is essentially suppressed. The shockwave treatment can then be started. If required, a synchronous pivoting of the patient bed together with the shockwave source 11 and/or of the x-ray diagnostics installation 29, around the common swiveling axis GS in the direction of the curved double arrow $\beta$ can ensue before or during the treatment to stabilize the position of a calculus to be disintegrated by the force of gravity. No dislocations whatsoever of the focal region F thereby occur. It is always guaranteed that the central ray ZS of the x-ray beam proceeds through the focal region F. It might at most be necessary to slightly correct the alignment of the patient relative to the shockwave source 11 by adjusting the patient bed 1, to take a potential change in the position of the calculus 26 into consideration.

Figure 5:
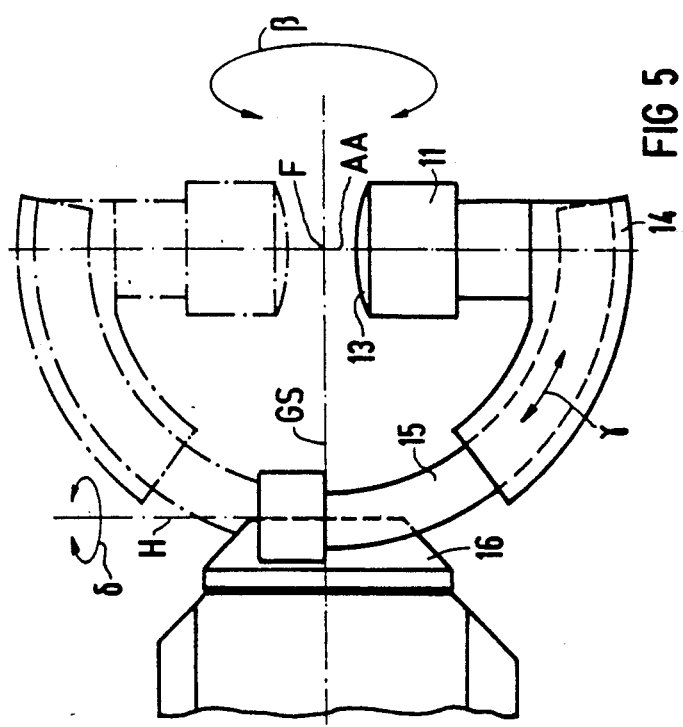
FIG. 5 is a schematic, partial view of the apparatus in the direction of the arrow C of FIG. 1 without patient bed that illustrates an operating condition deviating from FIG. 1.
Figure 6:
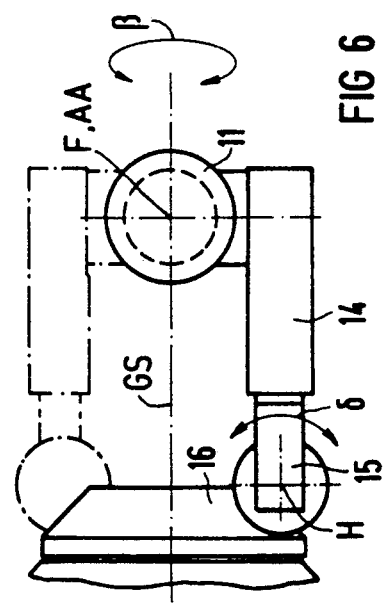
FIG. 6 shows the operating condition of FIG. 5 in a schematic, partial view of the apparatus in the direction of the arrow D in FIG. 1 without the patient beds.

There is also the possibility in the apparatus of FIGS. 8 through 11 of bringing the shockwave generator 11 into an under-table position, or into a standby position, in the same fashion as was already set forth with reference to FIGS. 5 through 7. Moreover, it can be expedient for certain treatment cases—departing from FIGS. 8 through 10—, to bring the x-ray radiator 30 into an under-table position and the x-ray image intensifier 31 into an above-table position. To this end, the C-arm 32 is pivoted by 180° around the common swiveling axis GS proceeding from the position shown in FIGS. 8 through 10. With reference to FIG. 8, the pivot motion of the C-arm 32 ensues counter-clockwise around the common swiveling axis GS. To prevent component parts of the x-ray diagnostics installation 29 from colliding with the patient bed 1, the patient bed 1—again with reference to FIG. 8—is adjusted into its outermost, right position in the direction of the double arrow x, and the C-arm 32 is additionally displaced in the direction of the curved double arrow ε so that the x-ray generator 32 is situated as close as possible to the holder 33. It is then possible to pivot the C-arm 32 past the left end of the patient bed 1 in FIG. 8 without collisions occurring. Before this, the carriage 7 is brought to a height such that the ground clearance required for the pivoting of the C-arm 32 is present.

The radii of the C-shaped carrier 15 and of the C-arm 32, moreover, deviate from one another by a dimension that the C-arm 32 such can be pivoted around the common swiveling axis GS above the C-shaped carrier 15, at least when the shockwave source 11 is placed in its radially innermost position in the direction of the double arrow u and the x-ray image intensifier 31 is placed in its radially outermost position in the direction of the double arrow w.

As a consequence of the fact that the center plane of the C-shaped carrier 15 proceeds at a distance from the common swiveling axis GS and the center plane of the C-arm 32 contains the common swiveling axis GS, an alignment of the x-ray diagnostics installation 29 and of the shockwave source 11 adapted to a particular treatment case will usually be capable of being found wherein the C-shaped carrier 15 is situated outside of the beam path of the x-ray diagnostics installation 29.

In the described exemplary embodiment, the shockwave source 11 and the x-ray diagnostics installation 29 are spherically adjustable around the focal region F as the isocenter lying on the common swiveling axis GS. The described, synchronous pivoting of the shockwave source 11 and/or of the x-ray diagnostics installation 29 together with the patient bed 1 around the common swiveling axis GS, however, is also possible without dislocation of the focal region F or of the central ray ZS even if adjustability of the shockwave source 11 and of the x-ray diagnostics installation 29 relative to the patient bed 1 is established relative to something other than an isocentric, and when the focal region F does not lie on the common swiveling axis GS, or the central ray ZS does not intersect the common swiveling axis GS. Embodiments are also possible wherein an isocentric adjustability of only the shockwave source 11 or of only the x-ray diagnostics installation 29 is provided.

The image generating and control electronics 23 and, if present, the x-ray generator 44 are connected to the control unit 18 or 46 with the operating unit 19 or 47 having additional operating elements and/or function available for purposes not related to the invention disclosed herein.

The disintegration of calculi has been described in the case of both exemplary embodiments. It is apparent that the apparatus of the invention can also be employed for treating other pathologies. Although further modifications and changes may be suggested by those skilled in the art, it is the intention of the inventors to embody within the patent warranted hereon all changes and modifications as reasonably and properly come within the scope of their contribution to the art.

We claim as our invention:

1. An apparatus for the treatment of a life form with focused shockwaves, said apparatus comprising:
    a patient bed;
    a shockwave source having an acoustic axis, said patient bed and said shockwave source constituting pivotable components;
    means for adjusting said shockwave source relative to said patient bed;
    means adapted for acoustically coupling shockwaves from said shockwave source into the body of a life form;
    means for converging said shockwaves in a focal region on said acoustic axis of the shockwave source; and
    means for supporting said pivotable components having a common swiveling axis around which said pivotable components are selectively pivotable independently of one another or synchronously.

2. An apparatus as claimed in claim 1 wherein said common swiveling axis proceeds substantially horizontally.

3. An apparatus as claimed in claim 1 wherein said swiveling axis proceeds substantially transversely relative to a longitudinal axis of the patient bed.

4. An apparatus as claimed in claim 1 wherein said common swiveling axis proceeds substantially horizontally and proceeds substantially transversely relative to a longitudincal axis of said patient bed.

5. An apparatus as claimed in claim 1, further comprising:
    locating means for locating a therapeutically relevant region in said life form, said locating means being a further pivotable component;
    means for adjusting said locating means relative to the other pivotable components; and
    said means for supporting also supporting said locating means so as to be pivotable around said common swiveling axis independently of the other pivotable components or synchronized with at least one of the other pivotable components.

6. An apparatus as claimed in claim 5 wherein said common swiveling axis proceeds substantially horizontally.

7. An apparatus as claimed in claim 5 wherein said swiveling axis proceeds substantially transversely relative to a longitudinal axis of the patient bed.

8. An apparatus as claimed in claim 5 wherein said common swiveling axis proceeds substantially horizontally and proceeds substantially transversely relative to a longitudincal axis of said patient bed.

9. An apparatus as claimed in claim 5, further comprising:
means for synchronously pivoting said patient bed and at least one of the other pivotable components, proceeding from a horizontal position of the patient bed, by at least 45° in at least one direction independently of the position of said at least one other apparatus component relative to said patient bed.

10. An apparatus as claimed in claim 5 wherein said means for supporting includes means for pivoting at least one of the other pivotable components by at least 180° relative to said patient bed, regardless of the position that the patient bed assumes relative to said common swiveling axis.

11. An apparatus as claimed in claim 5, wherein said means for adjusting said locating means is means for spherically adjusting said locating means around an isocenter independently of the other pivotable components, and wherein the therapeutically relevant region locatable with the locating means contains said isocenter.

12. An apparatus as claimed in claim 11 wherein said common swiveling axis proceeds through said isocenter.

13. An apparatus as claimed in claim 11 wherein said means for adjusting said locating means is a C-arm pivotable around said common swiveling axis, said C-arm having a center plane proceeding parallel to said common swiveling axis, and said locating means being attached to said C-arm so as to be adjustable along a circular path around said isocenter.

14. An apparatus as claimed in claim 5, wherein said means for adjusting said shock wave source is means for spherically adjusting said shockwave source around an isocenter independently of said patient bed, and wherein said focal region of said shockwaves contains said isocenter.

15. An apparatus as claimed in claim 14 wherein said common swiveling axis proceeds through said isocenter.

16. An apparatus as claimed in claim 14 wherein said means for adjusting said shockwave source is a C-arm pivotable around said common swiveling axis, said C-arm having a center plane proceeding parallel to said common swiveling axis, and said locating means being attached to said C-arm so as to be adjustable along a circular path around said isocenter.

17. An apparatus as claimed in claim 16, wherein said C-arm has a center plane proceeding parallel to said common swiveling axis, and wherein said shockwave source is attached to said C-arm with its acoustic axis proceeding parallel to said center plane and intersecting said common swiveling axis.

18. An apparatus as claimed in claim 5 wherein said means for adjusting said shockwave source is means for spherically adjusting said shockwave source around an isocenter independently of said patient bed and independently of said locating means, said focal region of said shockwaves containing said isocenter.

19. An apparatus as claimed in claim 5 wherein said means for adjusting said locating means is means for spherically adjusting said locating means around an isocenter independently of the other pivotable components, said therapeutically relevant region locatable with said locating means containing said isocenter, and wherein said means for adjusting said shockwave source is means for spherically adjusting said shockwave source around said isocenter independently of the other pivotable components, said focal region of said shockwaves containing said isocenter.

20. An apparatus as claimed in claim 5 wherein said means for adjusting said locating means is a first C-arm pivotable around said common swiveling axis, said first C-arm having a center plane proceeding parallel to said common swiveling axis and said locating means being attached to said first C-arm so as to be adjustable on a circular path around an isocenter, and wherein said means for adjusting said shockwave source is a second C-arm pivotable around said common swiveling axis, said second C-arm having a center plane proceeding parallel to said common swiveling axis and said shockwave source being attached to said second C-arm so as to be adjustable on a circular path around said isocenter, said first and second C-arms having different diameters so as to both be pivotable around said common swiveling axis without colliding.

21. An apparatus as claimed in claim 20, wherein each of said first and second C-arms has a surface, said respective surfaces facing each other when said C-arms are disposed parallel to each other, and said first and second C-arms each having a center plane, said center planes being differently spaced from said common swiveling axis so that a distance is present between said surfaces of said C-arms facing each other when said C-arms are aligned parallel to each other.

22. An apparatus as claimed in claim 20 wherein said second C-arm has a center plane, and wherein said second C-arm is pivotable to a standby position at which said center plane is disposed at substantially a right angle relative to said common swiveling axis.

23. An apparatus as claimed in claim 20 wherein said locating means comprises an x-ray source and a radiation receiver disposed at opposite free ends of said first C-arm, said x-ray source generating an x-ray beam having a central ray proceeding through said isocenter to said radiation receiver, and said apparatus further comprising a holder for said first C-arm and means for displacing said first C-arm in said holder along the circumference of said first C-arm so that said x-ray source and said radiation receiver are pivotable around said isocenter.

24. An apparatus as claimed in claim 23 wherein said first C-arm has a center plane containing said common swiveling axis, and wherein said second C-arm has a center plane disposed at a distance from said common swiveling axis, and wherein said shockwave source is attached to said second C-arm with its acoustic axis proceeding parallel to said center plane of said second C-arm and intersecting said central ray in said common swiveling axis.

25. An apparatus as claimed in claim 1 further comprising:
an L-shaped carrier for said patient bed, said L-shaped carrier having a first end mounted for pivoting around said common swiveling axis, and a second end to which said patient bed is attached cantilevered.

26. An apparatus as claimed in claim 1 wherein said shockwave source contains an ultrasound locating means for locating a theraputically relevant region.

* * * * *